United States Patent [19]

Frenzel

[11] Patent Number: 5,786,337
[45] Date of Patent: Jul. 28, 1998

[54] PROTECTIVE MEDIUM FOR PRESERVING VITAL TISSUE, ESPECIALLY TEETH

[75] Inventor: Bernd Frenzel, Berlin, Germany

[73] Assignee: Biochrom KG, Germany

[21] Appl. No.: 572,585

[22] Filed: Dec. 14, 1995

[30] Foreign Application Priority Data

Dec. 24, 1994 [DE] Germany ............... 4445769.3

[51] Int. Cl.$^6$ ................................................ A61K 38/00
[52] U.S. Cl. ................................................ 514/19; 435/41
[58] Field of Search ........................... 435/41; 514/19

[56] References Cited

U.S. PATENT DOCUMENTS 3,983,712  10/1976  Soder et al. ................. 62/65
4,802,853   2/1989  Krasner ..................... 433/215

FOREIGN PATENT DOCUMENTS 0556906  8/1993  European Pat. Off. .

OTHER PUBLICATIONS

Eagle, Science *130* (8/59) 432–437

Primary Examiner—Cecilia Tsang
Assistant Examiner—Bennett Celsa
Attorney, Agent, or Firm—Testa, Hurwitz & Thibeault, L.L.P

[57] ABSTRACT

The invention relates to an antibiotic-free protective medium, comprising nutrients for tissue growth, which comprises a non-antibiotic preservative to prevent contamination, a method of producing said protective medium and the use of said medium for preserving vital tissue.

12 Claims, 1 Drawing Sheet

PROTECTIVE MEDIUM FOR PRESERVING VITAL TISSUE, ESPECIALLY TEETH

FIELD OF THE INVENTION

The invention relates generally to a protective medium for preserving vital tissue, such as for example teeth which have been knocked out, and which medium can be sold in a ready-made form in a container. The invention particularly relates to a protective medium which in its liquid form is stable for at least one year and provides protection against undesired contaminating bacteria.

BACKGROUND OF THE INVENTION

Protective media have been developed for use in the transplantation of organs in human beings and in animals. Although these protective media are of extremely different compositions, they do have in common that at an organ temperature of 0°–10° C. they mostly should cause a rapid anaemia. This principle of hypothermic local anaemia has been tried and tested in the clinical field. (J. A. Wahlberg, J. H. Southard and F. O. Belzer, Cryobiology, 23, 477–482 (1986) "Development of a cold storage solution for pancreas preservation", G. M. Collins, M. B. Bravo-Shugarman and P. I. Terasaki, Lancet, 1219–1222 (1969)).

The Euro-Collins Solution or the University of Wisconsin (UW) Solution are examples of such protective media. Protective media outside the clinical field are for example required for preserving a tooth which has been broken off during an accident. It is essential to preserve the tooth or the like in a nutrient as otherwise the vital tissue adhering to the surface of the tooth root dries out in a short time and looses its capability to regenerate. It is possible by storing a tooth in a special protective medium, to reimplant the tooth even after 8 to 12 hours.

A medium of this type must provide protection against contamination, since a tooth which has been knocked out is generally contaminated with all kinds of bacteria and fungi. One test for developing such a medium is described in Published European Application No. EP-A2 0 353 345, wherein the dry agent is stored in an extremely costly container separate from the dissolving agent (water) and dissolved as required. The protection against contamination is achieved by adding antibiotics and fungicides. However, after a few weeks lumps occur in this solution and the extraordinarily hygroscopic dry agent decomposes. Consequently, it is not possible to guarantee that the dry agent is dissolved in the proper manner for use and the decomposition of the medium causes damage to the tissue being preserved. Moreover, the antibiotics and fungicides used to provide the protection against contamination only permit an extremely limited use within the scope of medical prescription. Furthermore, there is the constant danger of allergic reactions to the antibiotics. The ubiquitous storage process is therefore out of the question.

SUMMARY OF THE INVENTION

The object of the invention is to provide an antibiotic-free protective medium, comprising nutrients for tissue growth, which comprises a non-antibiotic preservative to prevent contamination. Another object of the invention is to ensure the longest possible stability, for example for one year, for this protective medium in the ready-made form.

The subject matter of the present invention is an antibiotic-free protective medium, comprising nutrients for tissue growth, which comprises as an anti-contaminant and preserving agent sodium azide ($NaN_3$) in a quantity of 5 to 60 mg/l.

DETAILED DESCRIPTION

Figure 1:
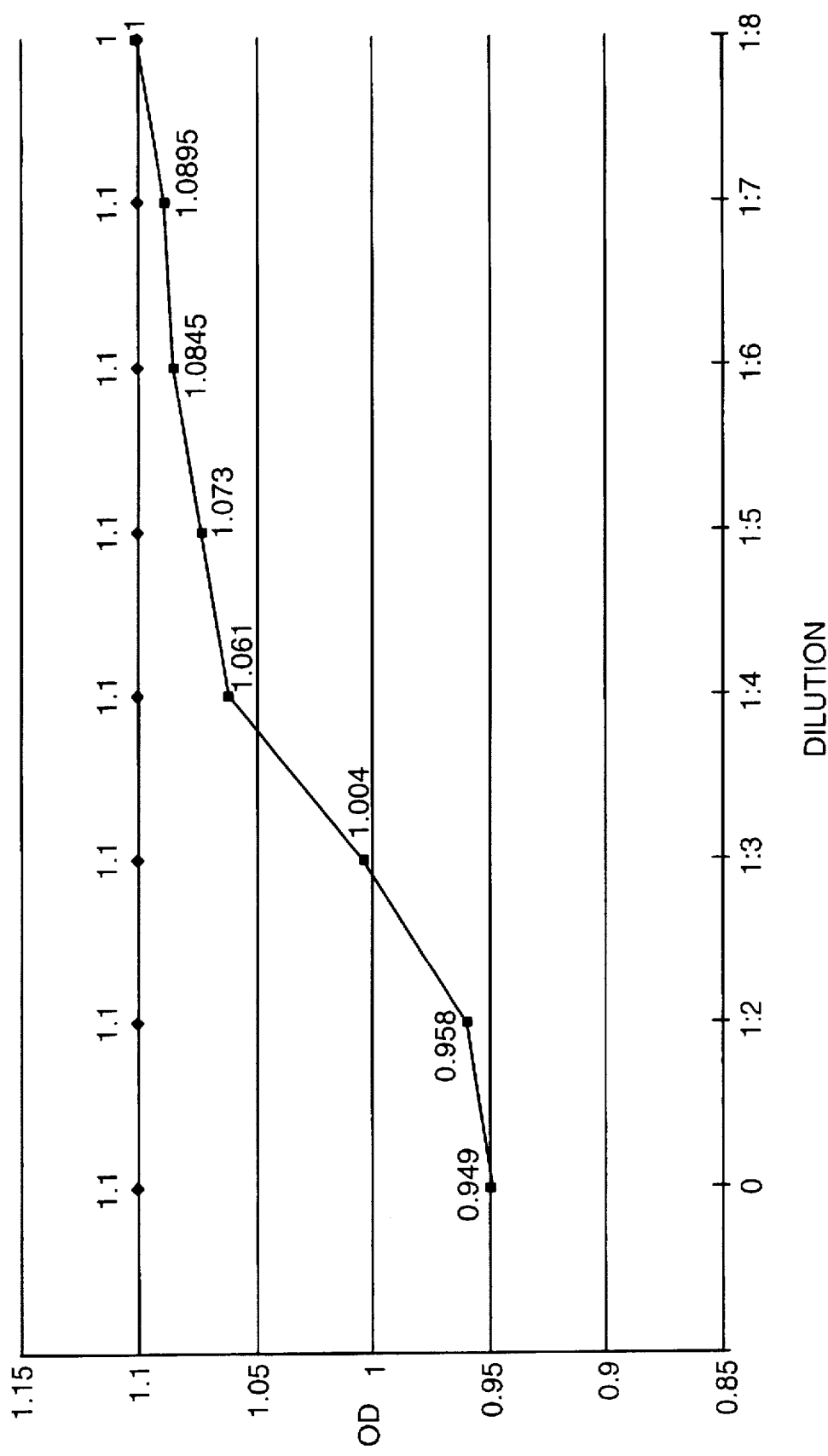
FIG. 1 shows cell culture growth with sodium azide.

Preferred embodiments are described below and in the subordinate claims.

When preparing a protective medium in accordance with the invention, the components are mixed in a dissolving agent under sterile conditions. The protective medium in accordance with the invention is in particular to be used for preserving vital tissue, especially teeth.

In contrast to the protective media described in the introduction, the protective medium in accordance with the invention comprises a plurality of necessary nutrients, in order to render it possible to store the tissue at room temperature, i.e. with metabolism. The critical ingredient for the stability of such a nutrient and protective medium is the necessary L-glutamine. It decomposes at room temperature in a short time, producing toxic ammoniac. Therefore, the L-glutamine used conventionally has been replaced in the protective medium in accordance with the invention by the dipeptide N-acetyl-L-alanyl-L-glutamine (ac-Ala-Gln). This is stable and can be stored for an extremely long period of time. It is naturally also possible to use other dipeptides or longer peptides of L-glutamine instead of the dipeptides described here. The protective medium containing the nutrient in accordance with the invention is produced under sterile conditions for example by combining the components in a dissolving agent, e.g. distilled water. It is understood from the term "sterile conditions", that either the starting materials are sterile or the protective medium is rendered sterile, for example by filtration through a bacteria-restraining filter, after combining the ingredients in a conventional manner. The following components can be present (quantities in mg/l). Possible concentration ranges are for example quoted in the right-hand column. Individual components can, however, be omitted in the protective medium in accordance with the invention.

| INGREDIENT | CONCENTRATION | RANGE |
| --- | --- | --- |
| NaCl | 6000 | 5000–8000 |
| KCL | 400 | 200–500 |
| $Na_2HPO_4.7H_2O$ | 1512 | 1000–2000 |
| $MgSO_4.7H_2O$ | 100 | 40–200 |
| $Ca(NO_3)_2.4H_2O$ | 100 | 60–120 |
| D-glucose | 2000 | 500–4000 |
| Phenol red | 5 | 1–10 |
| $NaHCO_3$ | 4000 | 1500–7000 |
| L-2-amino-5-guanidinovaleric acid | 200 | 100–300 |
| L-asparagine | 50 | 10–100 |
| L-aspartic acid | 20 | 5–50 |
| L-cystine | 50 | 10–100 |
| N-acetyl-L-alanyl-L-glutamine | 519 | 100–1000 |
| L-glutamic acid | 20 | 5–40 |
| Glycerol | 10 | 5–20 |
| L-histidine | 15 | 5–30 |
| L-hydroxyproline | 20 | 5–40 |
| L-isoleucine | 50 | 10–100 |
| L-leucine | 50 | 10–100 |
| L-lysine.HCl | 40 | 10–100 |
| L-methionine | 15 | 5–30 |
| L-phenylalanine | 15 | 5–30 |
| L-proline | 20 | 5–40 |
| L-serine | 30 | 10–60 |
| L-threonine | 20 | 5–40 |
| L-tryptophane | 5 | 1–10 |
| L-tyrosine | 20 | 5–40 |

| INGREDIENT | CONCENTRATION | RANGE |
| --- | --- | --- |
| L-valine | 20 | 5–40 |
| L(+)Ascorbic acid | 5 | 1–100 |
| Glutathione | 6 | 1–10 |
| Biotin | 0.2 | 0.01–2 |
| Vitamin $B_{12}$ | 0.005 | 0.001–1,01 |
| D-Ca-Pantothenate | 0.25 | 0.1–0.4 |
| Choline chloride | 3 | 1–5 |
| Folic acid | 1 | 0.5–3 |
| i-inositol | 35 | 10–50 |
| Nicotinamide | 1 | 01,–5 |
| p-aminobenzoic acid | 1 | 0.1–5 |
| Pyridoxin.HCl | 1 | 0.1–5 |
| Riboflavine | 0.2 | 0.02–0.8 |
| Thiamin.HCl | 1 | 0.1–5 |
| $NaN_3$ | 30 | 5–60 |

The particularly favourable concentration range for the preserving agent sodium azide amounts to 20 to 40 mg/l.

Antibiotics are added as anti-contaminants to all known nutrients which are used in cell culture (R. I. Freshney (Ed). In: Animal Cell Culture, Oxford University Press, Oxford, England pages 1–352 2nd Ed., (1992)). Surprisingly, it is evident that the antimicrobial medium sodium azide is tolerated in the cell culture. The cells not only survive the presence of sodium azide, but surprisingly they are even able to divide and grow. In the following test, the above described protective medium without $NaN_3$ with an additive of 10% fetal calf serum was added to an identical number of Hs68 cells for control purposes. In a further test series, the preserving agent sodium azide ($NaN_3$) was added. After an incubation period of 3 days in the incubator with 5% $CO_2$, the cells were coloured with crystal violet and the cell growth determined by measuring the OD values achieved in the ELISA reader.

The following concentrations of preserving media, which allow a preserving process, were used:

| DILUTING STAGES | SODIUM AZIDE MG/l |
| --- | --- |
| 0 | 40,00 |
| 1:2 | 20,00 |
| 1:3 | 13,33 |
| 1:4 | 10,00 |
| 1:5 | 8,00 |
| 1:6 | 6,67 |
| 1:7 | 5,71 |
| 1:8 | 5,00 |

The test results show that sodium azide surprisingly allows the cells to grow. (cf. FIG. 1)

| | CONTROL | SODIUM AZIDE OD |
| --- | --- | --- |
| 0 | 1.1 | 0.949 |
| 1:2 | 1.1 | 0.958 |
| 1:3 | 1.1 | 1.004 |
| 1:4 | 1.1 | 1.061 |
| 1:5 | 1.1 | 1.073 |
| 1:6 | 1.1 | 1.0845 |
| 1:7 | 1.1 | 1.0895 |
| 1:8 | 1.1 | 1.1025 |

The stability of such a nutrient was checked by means of the cell culture. The cell-maintaining, growth-promoting characteristics were determined in comparison to a control and the test repeated after a storage period of 18 months at room temperature. It was evident that the cell-maintaining and growth promoting characteristics of the medium remained unchanged even after 18 months.

What is claimed is:

1. An antibiotic-free protective medium comprising a protective tissue growth medium, a non-antibiotic preservative to prevent contamination, and a room temperature stable dipeptide wherein one amino acid of the dipeptide is L-glutamine, and wherein the preservative is sodium azide ($NaN_3$).

2. The protective medium according to claim 1 wherein the $NaN_3$ is present in a quantity of 5–60 mg/l.

3. The protective medium according to claim 1, wherein the $NaN_3$ is present in a quantity of 20–40 mg/l.

4. The protective medium according to claim 3, wherein the $NaN_3$ is present in a quantity of 30 mg/l.

5. The protective medium according to claim 1, wherein the dipeptide is N-acetyl-L-alanyl-L-glutamine.

6. A method for producing an antibiotic-free protective medium, comprising combining at room temperature a tissue growth medium with a non-antibiotic preservative to prevent contamination, a room temperature stable dipeptide wherein one amino acid of the dipeptide is L-glutamine, and a dissolving agent under sterile conditions, and wherein said preservative is $NaN_3$.

7. A method for preserving vital tissue comprising contacting said tissue with a composition comprising an antibiotic-free protective tissue growth medium, a non-antibiotic preservative to prevent contamination, and a room temperature stable dipeptide wherein one amino acid of the dipeptide is L-glutamine, and wherein said preservative is $NaN_3$.

8. The method according to claim 7, wherein the vital tissue is residual tissue on teeth.

9. The method of claim 7 wherein the dipeptide is N-acetyl-L-alanyl-L-glutamine.

10. A kit comprising a container having disposed therein an antibiotic-free protective tissue growth medium, an amount of $NaN_3$ capable of preventing contamination of the medium and a room temperature-stable dipeptide wherein one amino acid of the dipeptide is L-glutamine.

11. The kit of claim 10 wherein the concentration of $NaN_3$ is from 5 to 60 mg/l.

12. The kit of claim 10 wherein the dipeptide is N-acetyl-L-alanyl-L-glutamine.

* * * * *

UNITED STATES PATENT AND TRADEMARK OFFICE
CERTIFICATE OF CORRECTION

PATENT NO. : 5,786,337
DATED : July 28, 1998
INVENTOR(S) : Frenzel

It is certified that error appears in the above-identified patent and that said Letters Patent is hereby corrected as shown below:

On cover page, under: [30] Foreign Application Priority Data,
the filing date of German priority document no. 44 45 769.3 should be --Dec. 21, 1994-- not "Dec. 24, 1994".

Signed and Sealed this

Twenty-ninth Day of December, 1998

*Attest:*

BRUCE LEHMAN

*Attesting Officer*         *Commissioner of Patents and Trademarks*